United States Patent [19]

Hamill et al.

[11] 4,132,778

[45] Jan. 2, 1979

[54] ANTIBIOTIC A-32887

[75] Inventors: Robert L. Hamill, Greenwood; Marvin M. Hoehn, Indianapolis, both of Ind.

[73] Assignee: Eli Lilly and Company, Indianapolis, Ind.

[21] Appl. No.: 838,703

[22] Filed: Oct. 3, 1977

Related U.S. Application Data

[62] Division of Ser. No. 801,876, May 31, 1977.

[51] Int. Cl.$^2$ .............................................. A61K 35/00
[52] U.S. Cl. ................................... 424/121; 424/122
[58] Field of Search .............. 424/121, 122; 195/80 R

[56] References Cited

U.S. PATENT DOCUMENTS 3,705,238  12/1974  Hamill et al. ..................... 424/121

OTHER PUBLICATIONS

Westley et al., "CRC Handbook of Microbiology," vol. 3, CRC Press, Cleveland, Ohio, 1973, pp. 407–411.
Tsuji et al., J. Antibiotics, 29, pp. 10–14 (1976).
Derwent No. 44312v, Abstracting Japanese Kokai 9014-9692, 2-8-74.
Jones et al., J. Amer. Chem. Soc., 95, pp. 3399–3400 (1973).

Primary Examiner—Jerome D. Goldberg
Attorney, Agent, or Firm—Nancy J. Harrison; Arthur R. Whale

[57] ABSTRACT

Antibiotic A-32887 is produced by submerged aerobic fermentation of Streptomyces albus NRRL 11109. A-32887 is an antibacterial, antiprotozoal, anticoccidial, and insecticidal agent. A-32887 also increases feed-utilization efficiency in ruminants.

5 Claims, 6 Drawing Figures

ANTIBIOTIC A-32887

This is a division of application Ser. No. 801,876, filed May 31, 1977.

BACKGROUND OF THE INVENTION

1. Field of the Invention

New, improved antibiotics are continually in demand. In addition to antibiotics which are useful for human diseases, improved antibiotics are also needed in the veterinary field. Improved growth promotion in animals is one important goal for these antibiotics. Growth promotion is achieved, for example, by reducing disease and by increasing feed-utilization efficiency.

Coccidiosis is one disease important to veterinary science, especially to the poultry industry. Coccidiosis results from infection by one or more species of *Eimeria* or *Isopora* (for a summary see Lund and Farr in "Diseases of Poultry," 5th ed., Biester and Schwarte, Eds., Iowa State University Press, Ames, Iowa, 1965, pp 1056-1096). Economic losses due to coccidiosis are great, and known anticoccidial agents have many disadvantages. Improved anticoccidial agents continue to be needed.

Promotion of growth in ruminants, such as cattle, is another economically-desirable objective of veterinary science. Of particular interest is growth promotion which is achieved by increasing feed-utilization efficiency. The mechanism for utilization of the major nutritive portion (carbohydrates) of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Eds., Oriel Press, Newcastle-upon-Tyne, England, 1970, pp 408-410.

The relative efficiency of VFA utilization is discussed by McCullough in *Feedstuffs*, June 19, 1971, page 19; Eskeland et al. in *J. An. Sci.* 33, 282 (1971); and Church et al. in "Digestive Physiology and Nutrition of Ruminants," Vol. 2, 1971, pp 622 and 625. Although acetates and butyrates are utilized, propionates are utilized with greater efficiency. A beneficial compound, therefore, stimulates animals to produce a higher proportion of propionates from carbohydrates, thereby increasing carbohydrate-utilization efficiency.

2. The Prior Art

A-32887 is a new member of the group of polyether antibiotics. Examples of members of this group include monensin (U.S. Pat. No. 3,501,568); dianemycin [R. L. Hamill, M. M. Hoehn, G. E. Pittenger, J. Chamberlin, and M. Gorman, *J. Antibiotics* 22, 161 (1969)]; nigericin [L. K. Steinrauf, Mary Pinkerton, and J. W. Chamberlin, *Biochem. Biophys. Res. Comm.* 33, 29 (1968)]; salinomycin (U.S. Pat. No. 3,857,948); A-130-A (U.S. Pat. No. 3,903,264); A-28695 A and B (U.S. Pat. No. 3,839,558); grisorixin [*Chem. Commun.*, p. 1421 (1970)]; A-218 and K-41 [*J. Antibiotics* 29 (1), 10-14 (1976)].

Of this group of antibiotics, A-32887 is most closely related to K-41. A convenient method for distinguishing A-32887 from K-41 is by chromatography. A-32887 can be separated from K-41, for example, by silica-gel thin-layer chromatography in the following two systems ($R_f$ values are approximate):

| Antibiotic | Solvent System | $R_f$ Value |
|---|---|---|
| A-32887 | chloroform:methanol (92:8) | 0.78 |
| K-41 | chloroform:methanol (92:8) | 0.84 |
| A-32887 | ethyl acetate:ethanol (1:4) | 0.76 |
| K-41 | ethyl acetate:ethanol (1:4) | 0.70 |

SUMMARY OF THE INVENTION

This invention relates to an antibiotic substance which is produced by culturing a hitherto undescribed strain of the organism *Streptomyces albus* NRRL 11109.

The antibiotic substance of this invention is arbitrarily designated herein as A-32887. The $C_2$-$C_6$-acyl ester derivatives of antibiotic A-32887, the methyl ether derivative of antibiotic A-32887, and the pharmaceutically-acceptable salts of antibiotic A-32887 and of said ester and ether derivatives are also part of this invention. To simplify discussions of utility, the term "A-32887 compound" is used and refers to antibiotic A-32887, a specified acyl ester derivative of A-32887, the methyl ether derivative of A-32887 or a pharmaceutically-acceptable salt of A-32887 or of said ester or ether derivatives.

A-32887 is produced by culturing a novel strain of *Streptomyces albus*, NRRL 11109, under submerged aerobic fermentation conditions until a substantial level of antibiotic activity is produced. A-32887 is extracted from basified broth filtrate with polar organic solvents. The extracted A-32887 is purified by absorption chromatography.

A-32887 inhibits the growth of organisms which are pathogenic to animal and plant life. More specifically, A-32887 is an antibacterial, antifungal, antiprotozoal, anticoccidial, antiviral and insecticidal agent. In addition, A-32887 increases feed-utilization efficiency in ruminants, inhibits the enzyme ATPase, and is a blood-pressure-lowering agent.

DESCRIPTION OF THE DRAWINGS

The following infrared absorption spectra in chloroform are presented in the drawings.

DETAILED DESCRIPTION

The following paragraphs describe the properties of antibiotic A-32887.

A-32887 is a white, amorphous powder which melts at approximately 90° C. Elemental analysis of A-32887 indicates that it has the following approximate percentage composition (average): Carbon, 61.61%; Hydrogen, 8.56%; Oxygen, 28.63%. A-32887 has an approximate empirical formula of $C_{48-49}H_{80-86}O_{17-18}$ and a preferred empirical formula of $C_{48}H_{82}O_{18}$.

A-32887 has a molecular weight of about 946, as determined by mass spectrometry.

Figure 1:
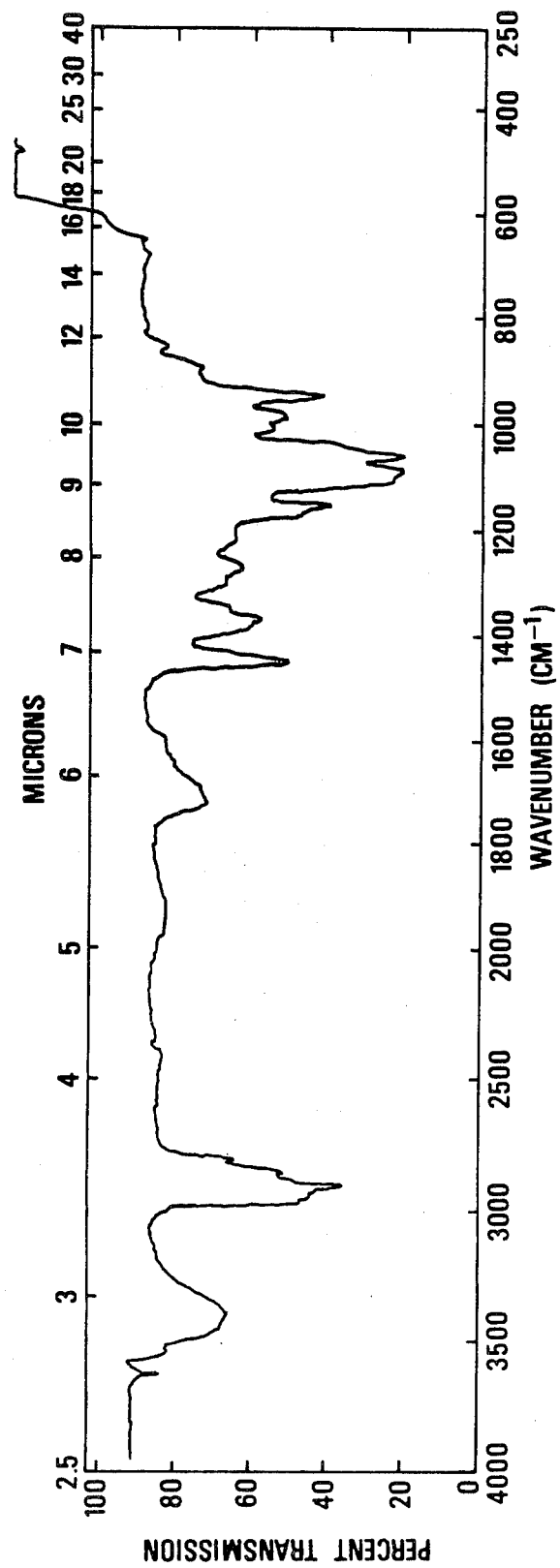
FIG. 1 — A-32887 (free acid)

The infrared absorption spectrum of A-32887 (free acid) in chloroform is shown in FIG. 1 of the accompanying drawings. Significant absorption maxima occur at the following frequencies (cm$^{-1}$): 3540 (shoulder), 3420 (medium), 2945 (shoulder), 2905 (strong), 2860 (shoulder), 2805 (shoulder), 1710 (weak), 1450 (medium), 1370 (medium), 1350 (shoulder), 1300 (shoulder), 1275 (weak), 1170 (shoulder), 1155 (medium), 1100 (shoulder), 1085 (strong), 1060 (strong), 1010 (weak), 990 (weak), 980 (shoulder), 948 (medium), 890 (weak), and 850 (weak).

The ultraviolet spectrum of A-32887 shows no significant absorption.

The proton-magnetic-resonance spectrum of A-32887 indicates the presence of five methoxyl groups.

A-32887 (free acid) has the following specific rotation: $[\alpha]_D^{25} + 15.9°$ (c 1, CHCl$_3$).

A-32887 mixed sodium-potassium salt crystallizes from acetone-water and has a melting point of about 187°–190° C. Elemental analysis of A-32887 Na-K salt indicates that it has the following approximate percentage composition (average): Carbon, 60.14; Hydrogen, 8.11%; Oxygen, 29.64%; Sodium, 2.31%; Potassium, 0.46%.

Figure 2:
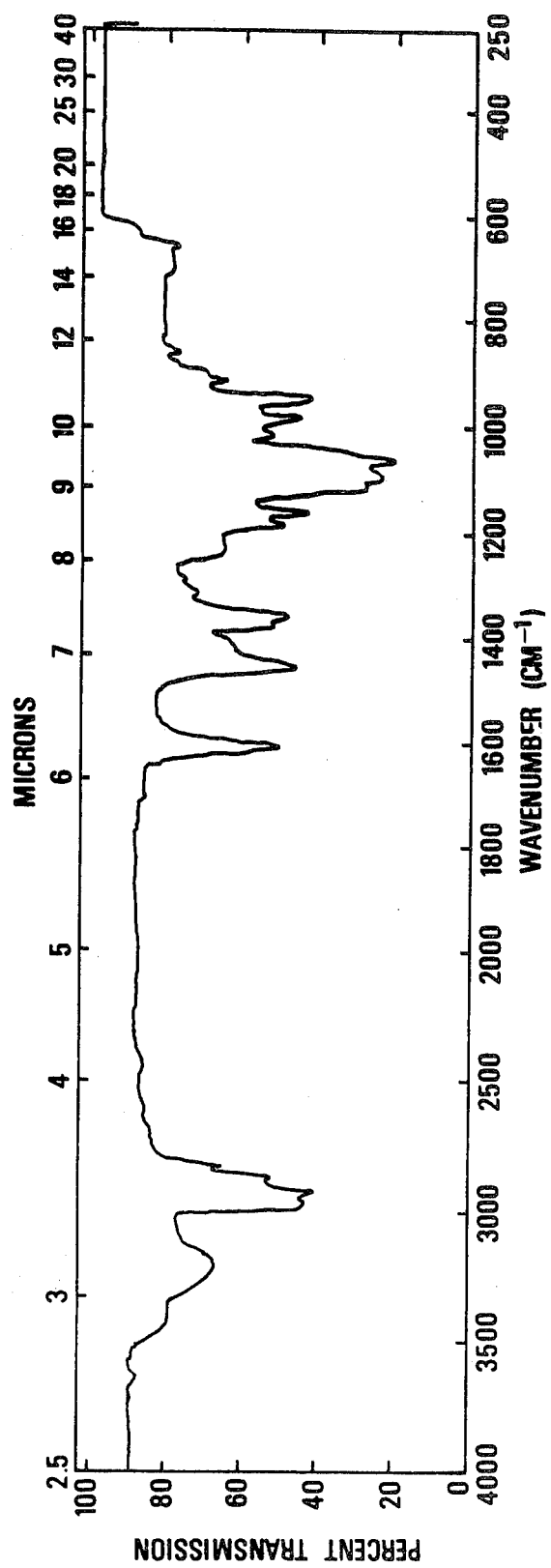
FIG. 2 — A-32887 mixed sodium-potassium salt
Figure 3:
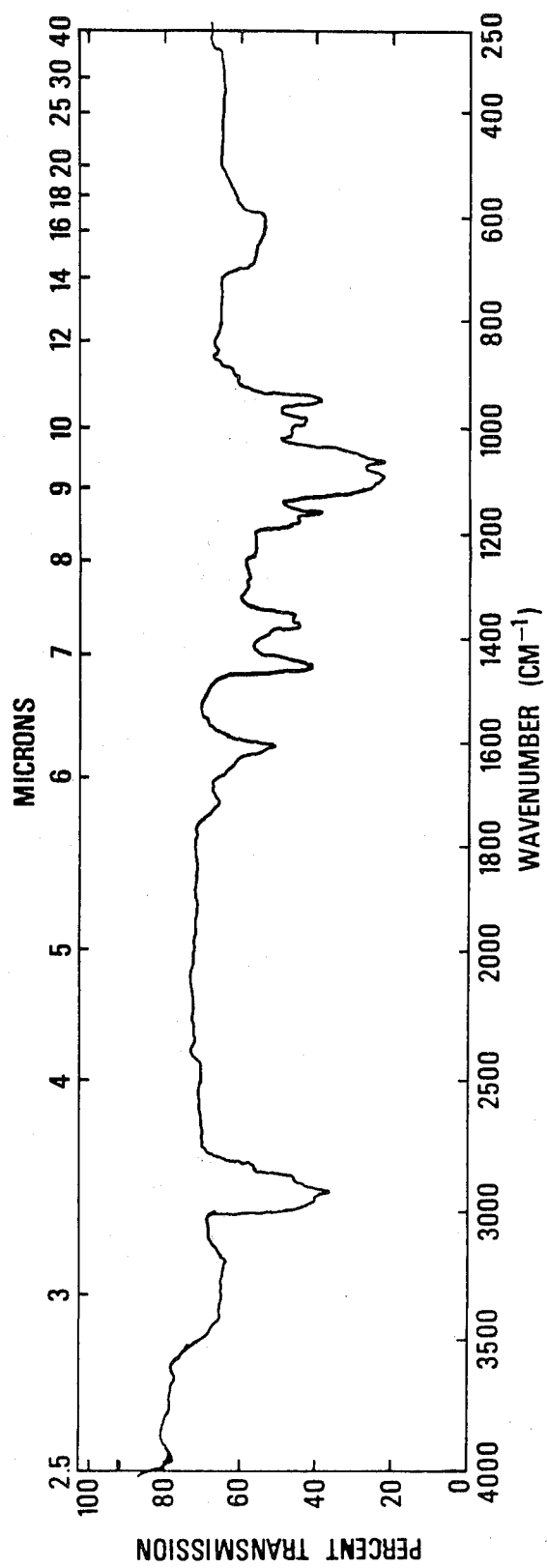
FIG. 3 — A-32887 sodium salt

The infrared absorption spectrum of A-32887 Na-K salt in chloroform is shown in FIG. 2 of the accompanying drawings. Significant absorption maxima are observed at the following frequencies (cm$^{-1}$): 3400 (shoulder), 3210 (medium), 2970 (strong), 2925 (strong), 2870 (weak), 2820 (weak), 1605 (medium), 1455 (medium), 1375 (shoulder), 1358 (medium), 1310 (weak), 1285 (weak), 1183 (medium), 1160 (medium), 1110 (shoulder), 1090 (strong), 1060 (strong), 1012 (weak), 980 (medium), 942 (medium), 910 (weak), 875 (shoulder), and 858 (weak).

A-32887 Na-K salt, crystallized from acetone-water, has the following characteristic X-ray powder diffraction pattern (CuNi, 1.5405 λ, d = interplanar spacing in angstroms):

| d | Relative Intensity |
|---|---|
| 12.53 | 50 |
| 10.10 | 100 |
| 9.5 | 40 |
| 9.05 | 40 |
| 8.07 | 70 |
| 7.16 | 100 |
| 6.77 | 100 |
| 6.48 | 70 |
| 6.16 | 60 |
| 5.58 | 50 |
| 5.35 | 50 |
| 5.10 | 30 |
| 4.86 | 60 |
| 4.70 | 50 |
| 4.44 | 50 |
| 4.25 | 50 |
| 4.06 | 40 |
| 3.80 | 30 |
| 3.68 | 40 |
| 3.58 | 30 |
| 3.42 | 60 |
| 3.22 | 10 |
| 3.06 | 10 |
| 2.97 | 10 |
| 2.85 | 10 |
| 2.76 | 02 |
| 2.61 | 15 |
| 2.49 | 05 |
| 2.47 | 05 |
| 2.44 | 15 |
| 2.36 | 10 |
| 2.29 | 10 |
| 2.20 | 02 |
| 2.12 | 02 |
| 2.03 | 05 |
| 1.96 | 05 |
| 1.90 | 02 |
| 1.81 | 02 |

A-32887 Na-K salt has the following specific rotation:

$[\alpha]_D^{25} + 9.6°$ (c 1, CHCl$_3$).

Electrometric titration of A-32887 in 80% aqueous dimethylformamide indicates the presence of a titratable group with a pK$_a$ value of 4.60.

A-32887 is soluble in a variety of organic solvents such as methanol, ethanol, dimethylformamide, dimethyl sulfoxide, ethyl acetate, chloroform, acetone, and benzene; is slightly soluble in non-polar organic solvents such as hexane and heptane; and is insoluble in water.

A-32887 is stable in aqueous solutions having a pH of from about 3 to about 11, but is unstable in solutions having a pH lower than about 3.

A-32887 sodium salt has a molecular weight of about 968, and A-32887 potassium salt has a molecular weight of about 984, both as determined by field-desorption (FD) mass spectrometry. The ion at m/e 969 (M + H) in the FD spectrum of A-32887 sodium salt was peak matched with a field-ionized mass standard. The found mass was 969.5373; the theoretical mass for C$_{48}$H$_{82}$O$_{18}$Na is 969.5399. This finding supports a molecular formula of C$_{48}$H$_{82}$O$_{18}$ for A-32887 free acid.

In the following paper-chromatographic systems, using *Bacillus subtilis* ATCC 6633 bioautography for detection, A-32887 has these approximate R$_f$ values:

| Solvent System | R$_f$ Value |
|---|---|
| Water saturated with methyl isobutyl ketone (MIBK) | 0.58 |
| Water:methanol:acetone (12:3:1). This solution is adjusted to pH 10.5 with NH$_4$OH and then lowered to pH 7.5 with H$_3$PO$_4$ | 0.32 |
| Propanol:water (1:9) | 0.85 |
| Methanol:propanol:water (6:2:1). Paper buffered with 0.75 M KH$_2$PO$_4$, pH 4.0. | 0.79 |
| Methanol:0.05 M sodium citrate at pH5.7 (7:3). Paper buffered with 0.05 M sodium citrate at pH 5.7. | 0.85 |
| Propanol:water (7:3) | 0.91 |

In the following silica-gel TLC systems, using either vanillin spray reagent or *Bacillus subtilis* ATCC 6633 bioautography for detection, A-32887 has the these approximate R$_f$ values:

| Solvent System | R$_f$ Value |
|---|---|
| Methanol | 0.80 |
| Ethyl acetate:ethanol (1:4) | 0.65 |
| Ethyl acetate:chloroform (1:1) | 0.36 |
| Ethyl acetate:chloroform (6:1) | 0.67 |
| Benzene:ethyl acetate:methanol (6:4:0.2) | 0.58 |

A-32887 has an acid function capable of forming salts and ester derivatives and has at least one hydroxyl group capable of esterification. The C$_2$–C$_6$-acyl ester derivatives of A-32887 and the pharmaceutically-acceptable salts of these ester derivatives are also useful as antibiotics and as agents which increase feed-utilization efficiency.

The A-32887 acyl ester derivatives are typically prepared by reacting A-32887 with the corresponding C$_2$–C$_6$-acid anhydride or acid chloride at room temperature.

The following paragraphs describe characteristics of typical A-32887 acyl ester derivatives.

A-32887 acetyl ester derivative (Na-K salt) is a white amorphous powder which has a molecular weight of about 988 and a melting point of about 127°–129° C. A-32887 acetyl ester derivative has an approximate empirical formula of $C_{50-51}H_{82-88}O_{18-19}$.

Figure 4:
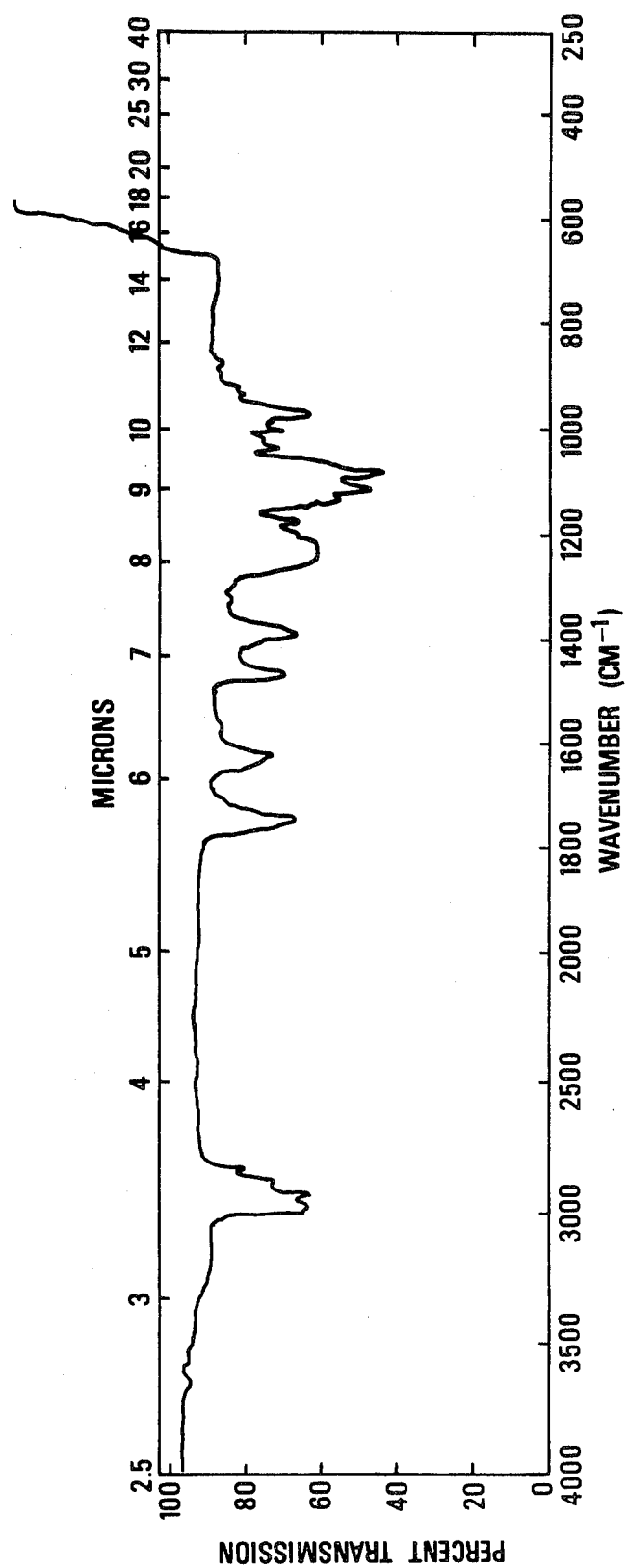
FIG. 4 — A-32887 acetyl ester derivative (Na-K salt)

The infrared absorption spectrum of A-32887 acetyl ester derivative (Na-K salt) in chloroform is shown in FIG. 4 of the accompanying drawings. Significant absorption maxima occur at the following frequencies ($cm^{-1}$): 3000, 2975, 2932, 2875, 2830, 1733, 1634, 1620, 1610, 1453, 1372, 1305, 1158, 1110, 1092, 1062, 1014, 996, 978, 948, 909, 893, and 853.

A-32887 n-butyryl ester derivative (Na-K salt) is a white amorphous powder which has a molecular weight of about 1016 and a melting point of about 59°–62° C. A-32887 n-butyryl ester derivative has an approximate empirical formula of $C_{52-53}H_{86-92}O_{18-19}$.

Figure 5:
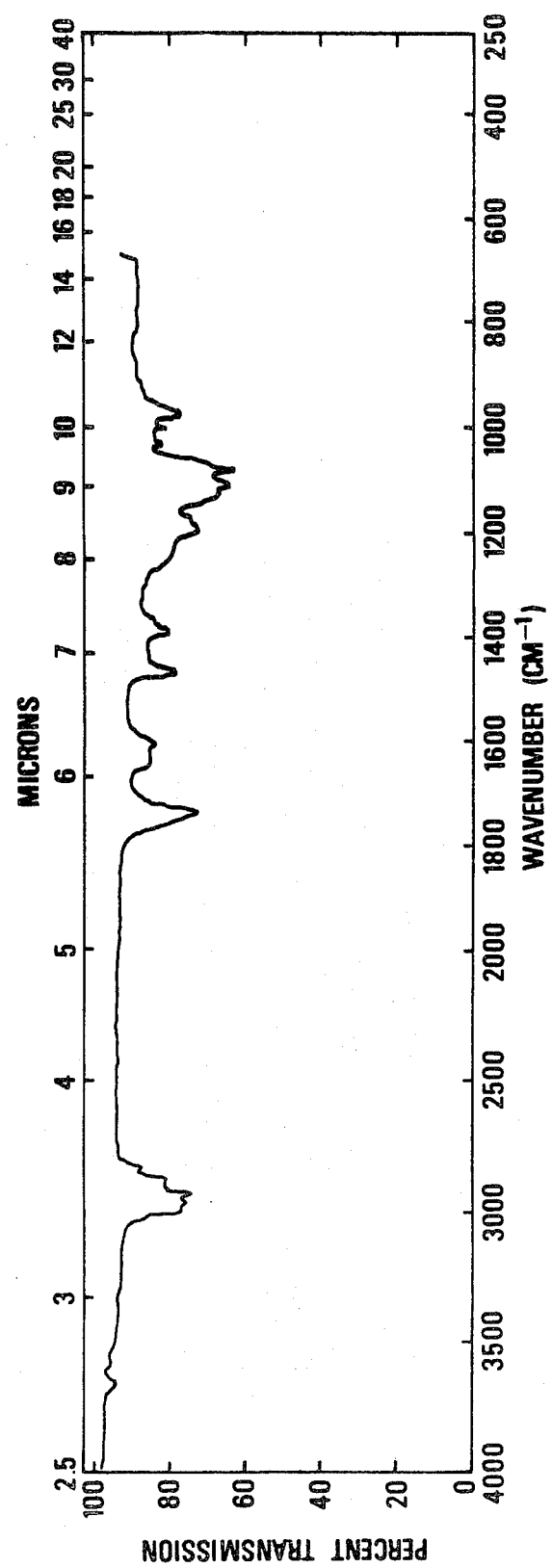
FIG. 5 — A-32887 n-butyryl ester derivative (Na-K salt)

The infrared absorption spectrum of A-32887 n-butyryl ester derivative (Na-K salt) in chloroform is shown in FIG. 5 of the accompanying drawings. Significant absorption maxima occur at the following frequencies ($cm^{-1}$): 3000, 2968, 2932, 2875, 2830, 1724, 1630, 1620, 1610, 1592, 1452, 1372, 1355, 1179, 1155, 1110, 1090, 1060, 1012, 977, 946, and 892.

The $C_2$–$C_6$-acyl ester derivatives of A-32887 are soluble in a variety of organic solvents such as methanol, ethanol, dimethylformamide, dimethyl sulfoxide, ethyl acetate, chloroform, acetone, and benzene; are slightly soluble in non-polar organic solvents such as hexane and heptane, and are insoluble in water.

A-32887 can be distinguished from its $C_2$–$C_6$ acyl ester derivatives by TLC. For example, the acetyl and n-butyryl ester derivatives can be separated from A-32887 by silica-gel TLC using a benzene:ethyl acetate (1:1) solvent system. A sulfuric acid spray reagent can be used for detection. In this system A-32887 and its acetyl and n-butyryl ester derivatives have the following approximate $R_f$ values:

|  | $R_f$ value |
|---|---|
| A-32887 (Na-K) | 0.47 |
| A-32887 acetyl ester derivative (Na-K) | 0.40 |
| A-32887 n-butyryl ester derivative (Na-K) | 0.64 |

The A-32887 hydroxyl group can react with lower alkanols, lower-alkyl thiols, and glycols to form ether derivatives using procedures similar to those described for the preparation of A204I derivatives in U.S. Pat. No. 3,907,832. The A-32887 $C_1$–$C_4$-alkyl ether derivatives and their pharmaceutically-acceptable salts are especially useful as antibiotics and as agents which increase feed-utilization efficiency. Of the $C_1$–$C_4$-alkyl ether derivatives, the methyl ether derivative of A-32887 and its pharmaceutically-acceptable salts are preferred.

A-32887 methyl ether derivative has an approximate empirical formula of $C_{49-50}H_{82-88}O_{17-18}$. The sodium salt of A-32887 methyl ether derivative is a white crystalline (n-hexane:ethyl acetate) compound having a melting point of about 214–216° C.

The molecular weight of A-32887 methyl ether derivative sodium salt is about 982; the molecular weight of A-32887 methyl ether derivative free acid is about 960 (both as determined by FD mass spectrometry).

Figure 6:
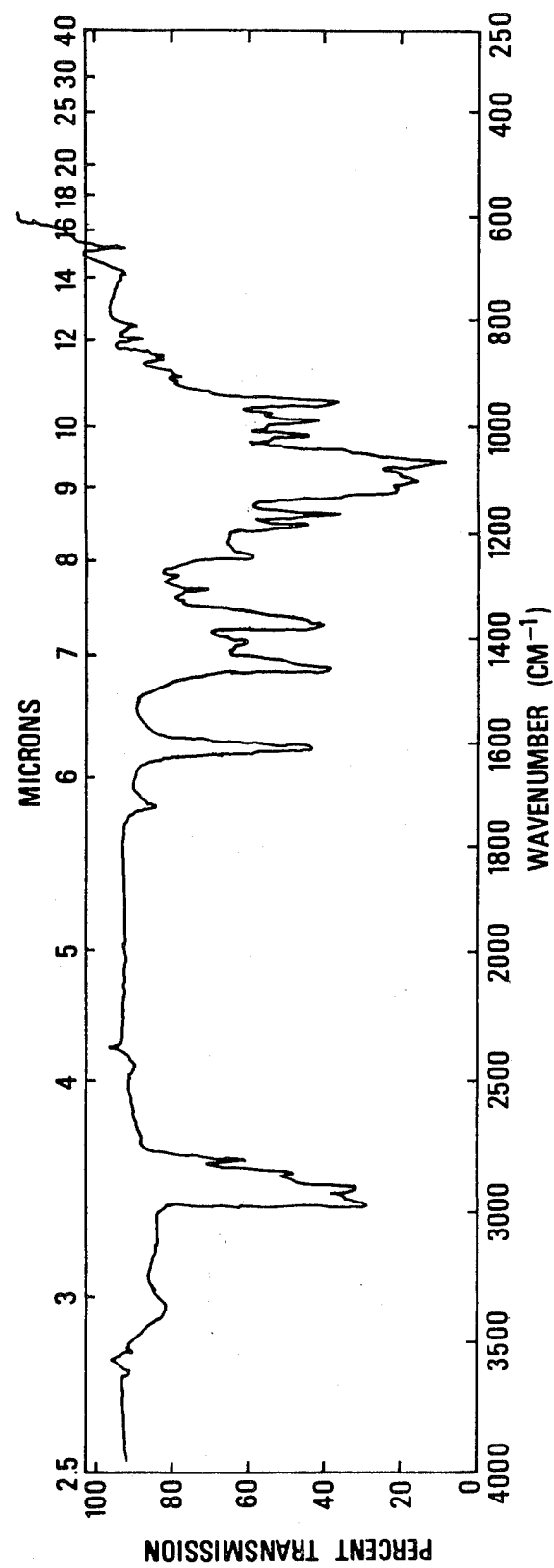
FIG. 6 — A-32887 methyl ether derivative (Na salt)

The infrared absorption spectrum of A-32887 methyl ether derivative (Na salt) in chloroform is shown in FIG. 6 of the accompanying drawings. Significant absorption maxima occur at the following frequencies ($cm^{-1}$): 3400 (broad), 2990, 2960, 2930, 2870, 2820, 1725, 1610, 1455, 1407, 1370, 1309, 1282, 1240, 1180, 1158, 1110, 1093, 1082, 1057, 1010, 980, 945, 900, 868, 858, 827, 802, 700, and 653.

The proton-magnetic-resonance spectrum of A-32887 methyl ether derivative (Na salt) indicates the presence of six methoxyl groups.

A-32887 methyl ether derivative (Na salt) has the following specific rotation: $[\alpha]_D^{25} - 5.1°$ (c 1, $CHCl_3$)

A-32887 methyl ether derivative (Na salt), crystallized from n-hexane:ethyl acetate, has the following characteristic X-ray powder diffraction pattern (CuNi, 1.5405 λ, d = interplanar spacing in angstroms):

| d | Relative Intensity |
|---|---|
| 13.18 | 50 |
| 12.01 | 50 |
| 9.02 | 100 |
| 8.26 | 100 |
| 7.19 | 80 |
| 6.46 | 50 |
| 5.78 | 20 |
| 5.46 | 20 |
| 5.00 | 30 |
| 4.24 | 20 |
| 3.72 | 20 |
| 3.36 | 05 |

Electrometric titration of A-32887 methyl ether derivative (Na salt) in 80% aqueous dimethylformamide indicates the presence of a titratable group with a $pK_a$ value of about 5.4.

A-32887 methyl ether derivative is soluble in a variety of organic solvents such as methanol, ethanol, dimethylformamide, dimethyl sulfoxide, ethyl acetate, chloroform, acetone, and benzene; is slightly soluble in non-polar organic solvents such as hexane and heptane; and is insoluble in water.

A-32887 methyl ether derivative (Na salt) can be separated from A-32887 (Na-K salt) by silica-gel TLC, using a benzene:ethyl acetate (1:1) solvent system and sulfuric acid spray reagent for detection. In this system, A-32887 and its methyl ether derivative have the following $R_f$ values:

|  | $R_f$ value |
|---|---|
| A-32887 (Na-K) | 0.425 |
| A-32887 methyl ether derivative (Na) | 0.22 |

A-32887, the $C_2$–$C_6$-acyl ester derivatives of A-32887, and A-32887 methyl ether derivative are capable of forming salts. The pharmaceutically-acceptable alkali-metal, alkaline-earth-metal and amine salts of A-32887, the $C_2$–$C_6$-acyl ester derivatives of A-32887, and A-32887 methyl ether derivative are also part of this invention. "Pharmaceutically-acceptable" salts are those in which the toxicity of the compound as a whole toward warm-blooded animals is not increased relative to the non-salt form. Representative and suitable alkali-metal and alkaline-earth metal salts of A-32887 include the sodium, potassium, lithium, cesium, rubidium, barium, calcium, and magnesium salts. Suitable amine salts of A-32887 include the ammonium and the primary, secondary, and tertiary $C_1$–$C_4$-alkylammonium and hydroxy-$C_2$-$C_4$-alkylammonium salts. Illustrative amine salts include those formed by reaction of A-32887 with ammonium hydroxide, methylamine, sec-butylamine, isopropylamine, diethylamine, di-isopropylamine, ethanolamine, triethylamine, 3-amino-1-propanol and the like.

The alkali-metal and alkaline-earth-metal cationic salts of A-32887 are prepared according to procedures commonly used for the preparation of cationic salts. For example, the free-acid form of A-32887 is dissolved in a suitable solvent such as acetone; a solution containing the stoichiometric quantity of the desired inorganic base in aqueous acetone is added to this solution. The salt thus formed can be isolated by routine methods, such as filtration or evaporation of the solvent.

The salts formed with organic amines can be prepared in a similar manner. For example, the gaseous or liquid amine can be added to a solution of A-32887 in a suitable solvent such as acetone; the solvent and excess amine can be removed by evaporation.

It is well known in the veterinary pharmaceutical art that the the form of an antibiotic is not ordinarily of great significance when treating an animal with the antibiotic. In most cases, conditions within the animal change the drug to a form other than that in which it was administered. The salt form in which it may be administered is, therefore, not of great significance. The salt form may, however, be chosen for reasons of economy, convenience, and toxicity.

A-32887 is produced by culturing an A-32887-producing strain of *Streptomyces albus* under submerged aerobic conditions in a suitable culture medium until substantial antibiotic activity is produced. A-32887 is separated from the culture medium by the use of various isolation and purification procedures understood in the art.

The new microorganism useful for the preparation of antibiotic A-32887 was isolated from a soil sample collected in Curacao in Dutch Antilles. This organism is classified as a strain of *Streptomyces albus* (Rossi-Doria) Waksman and Henrici. This classification is based upon a comparison with the published description of the neotype strain ATCC 3004 [A. J. Lyons, Jr., and T. G. Pridham, *J. Bacteriol.* 83, 370–380 (1962)] and the *Streptomyces albus* strain IMRU 3005 [S. A. Waksman, "The Actinomycetes, Vol. II, Classification, Identification and Descriptions of Genera and Species," The Williams and Wilkins Co., Baltimore, 1961].

This classification is based on methods recommended by the International Streptomyces Project [E. B. Shirling and D. Gottlieb, "Methods for Characterization of *Streptomyces* Species," *Intern. Bull. Systematic Bacteriol.* 16, 313–340 (1966)] along with certain supplementary tests.

Color names were assigned according to the ISCC-NBS method (K. L. Kelly and D. B. Judd, "The ISCC-NBS Methods of Designating Colors and a Dictionary of Color Names," U.S. Dept. of Commerce Circ. 553, 1955, Washington, D.C.). Figures in parentheses refer to the Tresner and Backus color series [H. D. Tresner and S. J. Backus, "System of Color Wheels for Streptomycete Taxonomy," *Appl. Microbiol.* 11, 335–338 (1963)]. Color tab designations are underlined. Maerz and Paul color blocks (A. Maerz and M. R. Paul, "Dictionary of Color," McGraw-Hill Book Co., Inc., New York, N. Y., 1950) are enclosed in brackets.

Cell walls were prepared by a modified method of Heymann et al., "Structure of Streptococcal Cell Walls. I. Methylation Study of C-Polysaccharide," *J. Biol. Chem.* 238(2):502–509 (1963). Amino acids were determined by automatic amino-acid analysis by the modified method of Spackman et al., *Anal. Chem.* 30:1190–1206. Cultures were grown at 30° C. unless otherwise noted.

CHARACTERISTICS OF A-32887-PRODUCING STRAIN

Morphology

Spiralled sporophores are produced. These are usually short. Although some chains have 3–10 spores per chain, there are usually more than 10 spores per chain. Spores are spherical to slightly oval and measure 0.78 $\mu$ × 0.56 $\mu$ with a range in size of 0.625 $\mu$ × 0.5 $\mu$ to 0.625 $\mu$. The spores are smooth, as observed by electron micrographs. Morphologically, culture A-32887 could be confused with a verticillate type of morphology in which the branches are equidistant; however, the morphology actually is of a type in which the branching is very irregular.

TABLE I

| CULTURAL CHARACTERISTICS ON VARIOUS MEDIA | |
|---|---|
| Medium | Characteristics |
| Czapek's-Solution Agar. | Abundant growth; reverse moderate yellow [11K3]; abundant sporulation and aerial mycelium; (W) a white; no soluble pigment. |
| ISP Medium #2 (Yeast-Extract—Malt-Extract Agar) | Abundant growth; reverse moderate yellow [11K3]; abundant sporulation and aerial mycelium; (W) a white; no soluble pigment. |
| Tryptone—Yeast Agar. | Scant growth; reverse pale yellow [11C1]; scant sporulation and aerial mycelium; (W) a white; no soluble pigment. |
| Nutrient Agar | Good growth; reverse pale yellow [11C1]; good aerial mycelium and sporulation; (W) a white; no soluble pigment. |
| V-8 Juice—Dextrose Agar | Abundant growth; reverse moderate yellowish brown [14E7]; abundant aerial mycelium and sproulation; (W) a white; no soluble pigment. |
| Glucose—Asparagine Agar | Good growth; reverse pale yellow [11O2]; good aerial mycelium and sporulation; (W) a white; no soluble pigment. |
| Tomato-Paste—Oatmeal Agar | Abundant growth; reverse grayish yellow [12D3]; abundant aerial mycelium and sporulatin; (W) a white to (Y) 2 ba pale yellow; no soluble pigment. |
| Emerson's Agar | Abundant growth; reverse light yellow brown [1217]; abundant aerial mycelium and sporulation ; (W) a white to (GY) 2dc yellowish gray; no soluble pigment. |
| ISP Medium #5 (Glycerol—Asparagine Agar) | Scant growth; no color assignment due to poor growth. |

TABLE I-continued
CULTURAL CHARACTERISTICS ON VARIOUS MEDIA

| Medium | Characteristics |
|---|---|
| Salts—Starch Agar | Good growth; reverse pale yellow [10B2]; good aerial mycelium ad sporulation; (W) a white; no soluble pigment. |
| ISP Medium #4 (Inorganic-Salts—Starch Agar) | Scant-to-fair growth; reverse pale yellow [9D2]; scant aerial mycelium and sporulation; (W) a white; some clearing by area where inoculated; no soluble pigment. Growth not confluent but principally as isolated colonies. |
| ISP Medium #3 (Oatmeal Agar) | Abundant growth; reverse pale yellow [10F2]; abundant aerial mycelium and sporulation; (W) a white; no soluble pigment. |
| Bennett's Modified(-COCl$_2$) Agar | Good-to-abundant growth; reverse pale yellow [11B2]; abundant aerial mycelium and sporulation; (W) a white to (GY) 2dc yellow-gray; no soluble pigment. |
| Glycerol—Glycine Agar | Good growth; reverse pale yellow [11B2]; scant aerial mycelium and sporulation; (W) a white; no soluble pigment. |
| Tyrosine Agar | Fair-to-good growth; reverse grayish yellow [12B3]; fair-to-good aerial mycelium and sporulation; (W) a white; no soluble pigment. |
| Calcium-Malate Agar | Good growth; reverse pale orange yellow; good aerial mycelium and sporulation; (W) a white; no soluble pigment. |

The organism was studied for selected physiologically properties in accordance with standard procedures. The properties observed and characteristics found are given in Table II:

TABLE II

| Property Observed | Characteristics |
|---|---|
| Action on Skim Milk | No change after 14 days. A soft curd is formed after 10 days incubation, but milk is not cleared. |
| Starch Hydrolysis | Starch hydrolyzed |
| Nitrate Reduction | Negative |
| Gelatin Liquefaction | None at 14 days |
| Melanin Pigment Production on: | |
| 1. Tryptone—Yeast-Extract Broth. | Negative |
| 2. Peptone—Yeast-Extract—Iron Agar. | Negative |
| 3. Tyrosine Agar | Negative |
| Growth on: | |
|    Carrot slice | Scant vegetative growth. |
|    Potato slice | Abundant growth and sporulation; aerial and spores off-white to brownish gray. |
| Temperature Requirements (Bennett's-agar slants; incubated 9 days) | 20° - No growth.<br>25° - Good growth; white aerial-reverse yellow brown; no soluble pigment.<br>30° - Good growth; white aerial-reverse yellow brown; no soluble pigment.<br>37° - Good growth; white aerial-reverse yellow brown; no soluble pigment.<br>43° - Fair growth; scant white aerial-reverse color darker than at 25°, 30° and 37° - brown; brown soluble pigment.<br>49° - No growth.<br>55° - No growth. |

The response of the culture to varying levels of sodium chloride, using Bennett's modified agar, is summarized in Table III.

TABLE III

| Percent NaCl in Medium | Characteristics |
|---|---|
| 1 | Good-to-abundant growth; aerial mycelium and spores; white aerial. |
| 2 | Abundant growth; abundant aerial mycelium and spores; white aerial. |
| 3 | Abundant growth; abundant aerial mycelium and spores; white aerial. |
| 4 | Abundant growth; abundant aerial mycelium and spores; white aerial. |
| 6 | Good-to-abundant growth; abundant aerial mycelium and spores; white aerial. |
| 8 | Good veg. growth; no aerial mycelium. |
| 10 | Fair-to-good veg. growth; no aerial mycelium. |
| 12 | Scant growth; no aerial mycelium. |
| 14 | Scant-to-no growth; no aerial mycelium. |

The results of carbon-utilization tests carried out with the organism are set forth in Table IV. The following symbols are used:

+ = Positive utilization
(+) = Probable utilization
(−) = Questionable utilization
− = No utilization

TABLE IV

| Carbon Source | Response |
|---|---|
| L-arabinose | + |
| D-ribose | (+) |
| D-xylose | (+) |
| D-galactose | (+) |
| D-glucose | (+) |
| D-mannose | (+) |
| D-fructose | (+) |
| L-sorbose | − |
| cellobiose | (+) |
| lactose | (+) |
| maltose | + |
| melibiose | (−) |
| sucrose | (+) |
| turanose | (−) to − |
| trehalose | + |
| melezitose | (−) |
| raffinose | (−) to − |
| dextrin | + |
| salicin | − |
| starch (soluble) | + |
| fucose | (+) |
| rhamnose | + |
| glucosamine | (+) |
| α-methylglucoside | − |
| α-methylxyloside | − |
| adonitol | (+) |
| dulcitol | (+) to − |
| i-erythritol | (+) |
| glycerol | (+) |
| i-inositol | + |
| mannitol | + |
| sorbitol | + |
| -Carbon (Negative Control) | − |

Cell Wall Studies

Using hydrolyzed whole cells of the organism, the presence of certain diagnostic sugars was determined. Isolated cell walls were used to determine the isomers of diaminopimelic acid and the amino-acid content. The results of these cell-wall studies are set forth below:

| Test | Result Observed |
|---|---|
| Isomers of diamino-pimelic acid | LL-isomer |
| Diagnostic sugars | No characteristic pattern |
| Amino-acid content | Major amounts of glutamic acid, glycine, alanine, and tyrosine. |

Certain characteristics of the A-32887-producing *S. albus* strain differ from those in the published description of *S. albus* (Rossi-Doria) Waksman and Henrici, supra. A comparison of the characteristics of the A-32887-producing strain (NRRL 11109) with those in the published description is given in Table V; differing characteristics are highlighted by an asterisk.

TABLE V

| Medium; Condition | Reaction of A-32887 *S. albus* NRRL 11109 | Published Description of *Streptomyces albus* |
|---|---|---|
| ISP Medium #2 (Yeast—Malt-Extract Agar) | White aerial; moderate yellow reverse | White or yellow aerial; yellow brown reverse |
| ISP Medium #3 (Oatmeal Agar) | White aerial; pale yellow reverse | White aerial; yellow brown reverse |
| ISP Medium #4 (Inorganic-Salts—Starch Agar) | White aerial; pale yellow reverse | White aerial; yellow brown reverse |
| ISP Medium #5 (Glycerol Asparagine Agar) | Scant growth; no color assignment | White or yellow aerial; yellow brown reverse |
| Reacton to various levels of NaCl | Tolerates levels of up to 12%. No growth at 14%. | Tolerates levels greater than 13%. No growth at 15% |
| Temperature Requirements | Optimum growth at 25° – 43° C | Optimum growth at 25° – 44° C |
| Reaction to the following carbon sources: | | |
| D-Glucose | (+) | + |
| D-Mannitol | + | + |
| D-Galactose | (+) | + |
| L-Arabinose* | + | − |
| Rhamnose* | + | − |
| D-Xylose | (+) | + |
| i-Inositol* | + | − |
| D-Fructose | (+) | ± |
| Salicin* | − | + |
| Raffinose | (−) | − |
| Whole-cell Hydrolysates | LL-diaminopimelic acid | LL-diaminopimelic acid |
| Nitrate Reduction* | Negative | Positive |
| Gelatin Liquefaction* | None at 14 days | Strong liquefaction |
| Melanin-pigment Production | Negative | Negative |
| Action on Skim Milk* | No change after 14 days. Soft curd is formed after 10 days, but milk is not cleared. | Rapid peptonization |
| Morphology | Spiralled | Spiralled |
| Spore ornamentation | Smooth | Smooth |

The *Streptomyces albus* culture useful for the production of antibiotic A-32887 has been deposited and made a part of the stock culture collection of the Northern Regional Research Center, Agricultural Research Service, U.S. Department of Agriculture, Peoria, Ill. 61604, from which it is available to the public under the number NRRL 11109.

As is the case with other organisms, the characteristics of the A-32887-producing culture, *Streptomyces albus* NRRL 11109, are subject to variation. For example, artificial variants and mutants of the NRRL 11109 strain may be obtained by treatment with various known mutagens such as ultraviolet rays, X-rays, high-frequency waves, radioactive rays, and chemicals. All natural and artificial variants and mutants which have the essential identifying characteristics of *Streptomyces albus* and produce A-32887 may be used in this invention. "Essential identifying characteristics" are those characteristics which are sufficient to classify an organism as *Streptomyces albus* NRRL 11109. One of these characteristics, of course, is the ability of the organism to produce A-32887. It will be understood by those skilled in the art that certain non-critical differences between the characteristics exhibited by a given organism and those identifying a reference organism can exist without affecting the classification of both such organisms as belonging to the same genus, species and strain.

The culture medium employed to grow *Streptomyces albus* NRRL 11109 can be any one of a number of media. For economy in production, optimal yield, and ease of product isolation, however, certain culture media are preferred. Thus, for example, a preferred carbohydrate source in large-scale fermentation is glucose, although dextrin, starch, maltose, and the like can also be used. A preferred nitrogen source is meat peptone, although other peptones, enzyme-hydrolyzed casein, soybean meal, amino acids and the like are also useful. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other substituents of the medium in amounts sufficient to meet the growth requirements of the organism. It may be necessary to add small amounts (i.e. 0.2 ml/l.) of an antifoam agent such as polypropylene glycol (M.W. about 2000) to large-scale fermentation media if foaming becomes a problem.

For production of substantial quantities of antibiotic A-32887, submerged aerobic fermentation in tanks is preferred. Small quantities of antibiotic A-32887 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that employed for larger fermentations, but other media can also be employed.

The A-32887-producing organism can be grown at temperatures between about 22° and about 45° C. Optimum A-32887 production appears to occur at temperatures of about 30° C.

As is customary in aerobic submerged culture processes, sterile air is blown through the culture medium. For efficient production of antibiotic A-32887 the volume of air employed in tank productions is preferably about 0.25–0.5 volume of air per volume of culture medium per minute (V/V/M).

Production of antibiotic A-32887 can be followed during the fermentation by testing samples of the broth or of extracts of the mycelial solids for antibiotic activity against organisms known to be sensitive to this antibiotic. One assay organism useful in testing this antibiotic is *Bacillus subtilis* ATCC 6633. The bioassay is conveniently performed by paper-disc assay on agar plates.

Following its production under submerged aerobic fermentation conditions, antibiotic A-32887 can be recovered from the fermentation medium by methods employed in the fermentation art. Although the antibiotic activity produced during fermentation of the A-32887-producing organism occurs in both the broth and in the mycelial mass, the major part of the activity is in the filtered broth. Maximum recovery of antibiotic A-32887 is accomplished, therefore, by an initial filtration to separate the broth from the mycelial mass. The filtered broth can then be further purified to give antibiotic A-32887. A variety of techniques may be used in this purification. A preferred technique for purification of the filtered broth involves adjusting the broth to about pH 9 and extracting with a suitable solvent such as ethyl acetate. The extracting solvent can then be evaporated under vacuum to give partially-purified antibiotic A-32887. Further purification of A-32887 involves the use of chromatography. A preferred adsorbent for this purification is silica gel.

Alternatively, the culture solids, including medium constituents and mycelium can be used without extraction or separation, but preferably after removal of water, as a source of antibiotic A-32887. For example, after production of A-32887 antibiotic activity, the whole fermentation broth or the broth filtrate can be dried by lyophilization, by drum-drying, or by azeotropic distillation and drying. The dried whole broth or dried broth filtrate can then be mixed directly into feed premix.

Antibiotic A-32887 inhibits the growth of pathogenic bacteria, especially gram-positive bacteria. Table VI summarizes the minimal inhibitory concentrations (MIC), as measured by standard agar-dilution assays, at which A-32887 (Na-K salt) inhibits certain bacteria.

TABLE VI

| Test Organism | MIC (mcg/ml) |
| --- | --- |
| Staphylococcus aureus 3055 | 6.25 |
| Streptococcus faecalis | 6.25 |
| Staphylococcus sp. | 1.56 |
| Streptococcus sp. | 3.12 |
| Pasteurella multocida (bovine) | 50.00 |
| Pseudomonas sp. | 3.12 |

The activity of A-32887 (Na-K salt) against illustrative bacteria, as measured by the conventional disc-diffusion method, is summarized in Table VI.

TABLE VII

| Test Organism | mcg/disc | Zone of Inhibition (mm) |
| --- | --- | --- |
| Staphylococcus aureus 3055 | 300 | 15.6 |
| Staphylococcus aureus 3055 | 30 | 12.0 |
| Staphylococcus aureus 3074* | 300 | 16.0 |
| Staphylococcus aureus 3074* | 30 | 12.7 |
| Staphylococcus aureus 3130** | 300 | 15.2 |
| Staphylococcus aureus 3130** | 30 | 15.0 |
| Streptococcus pyogenes (Group A) | 300 | 17.5 |
| Streptococcus pyogenes (Group A) | 30 | 14.0 |
| Streptococcus sp. (Group D) | 300 | 14.7 |
| Streptococcus sp. (Group D) | 30 | 13.7 |
| Diplococcus pneumoniae | 300 | 18.0 |
| Diplococcus pneumoniae | 30 | 16.0 |

*Penicillin G-resistant
**Methicillin-resistant

The antimicrobial activity of two typical A-32887 acyl ester derivatives is compared with that of A-32887 (each as Na-K salts) in Table VIII. Activity against illustrative bacteria is measured by the conventional disc-diffusion method. In addition, the results of a conventional paper-disc agar-diffusion assay system (Plate Assay) against *Bacillus subtilis* ATCC 6633 are reported. The activity in this test is quantitated and uses a dried-broth reference standard which is assigned an arbitrary potency of 100 units/ml. The samples were assayed at 1 mg/ml.

TABLE VIII

| Compound | Plate Assay units/ml | Staphylococcus aureus | Bacillus subtilis | Micrococcus lutea | Bacillus subtilis* |
| --- | --- | --- | --- | --- | --- |
| A-32887 | 1350 | 16 | 18 | 16 | 30 |
| A-32887 Acetyl Ester Derivative | 238 | trace | 12 | trace | 22 |
| A-32887 n-Butyryl Ester Derivative | 1109 | 14 | 16 | 12 | 27 |

*Minimal media

In one important aspect, the A-32887 compounds inhibit the growth of anaerobic bacteria. Table IX summarizes the MIC's at which A-32887 (Na-K salt) inhibits various anaerobic bacteria, as determined by standard agar-dilution assay. End points were read after 24-hour incubation.

TABLE IX

| Test Organism | MIC (mcg/ml) |
| --- | --- |
| Actinomyces israelii | ≦0.5 |
| Clostridium perfringens | ≦0.5 |
| Clostridium septicum | ≦0.5 |
| Eubacterium aerofaciens | ≦0.5 |
| Peptococcus asaccharolyticus | ≦0.5 |
| Peptococcus prevoti | ≦0.5 |
| Peptostreptococcus anaerobius | ≦0.5 |

TABLE IX-continued

| Test Organism | MIC (mcg/ml) |
|---|---|
| *Peptostreptococcus intermedius* | 1.0 |
| *Propionibacterium acnes* | ≤0.5 |
| *Bacteriodes fragilis* ssp *fragilis* 111 | 2 |
| *Bacteriodes fragilis* ssp *fragilis* 1877 | 2 |
| *Bacteriodes fragilis* ssp *fragilis* 1936B | 2 |
| *Bacteriodes fragilis* ssp *thetaiotaomicron* | 2 |
| *Bacteriodes melaninogenicus* 1856/28 | 32 |
| *Bacteriodes melaninogenicus* 2736 | 2 |
| *Bacteriodes vulgatis* | 4 |
| *Bacteriodes corrodens* | 2 |
| *Fusobacterium symbiosum* | 32 |
| *Fusobacterium necrophorum* | 32 |

The activity of the A-32887 compounds against anaerobic bacteria, especially against *Clostridium perfringens*, suggests that the A-32887 compounds would be beneficial in the treatment or prevention of enteritis in chickens, swine, cattle, sheep, and goats and in the treatment or prevention of enterotoxemia in ruminants.

Activity against mycoplasma is another useful aspect of the antimicrobial activity of the A-32887 compounds. Mycoplasma species, also known as pleuropneumonia-like (PPLO) organisms, are pathogenic to man and various animals. Anti-mycoplasma agents are especially needed by the poultry industry. The MIC's of A-32887 (Na-K salt) against typical mycoplasma species, as determined by in vitro broth-dilution studies, are summarized in Table X:

TABLE X

| Test Organism | MIC (mcg/ml) |
|---|---|
| *Mycoplasma gallisepticum* | 12.5 |
| *Mycoplasma synoviae* | 3.12 |
| *Mycoplasma hyorhinis* | 25.0 |
| *Mycoplasma hyopneumoniae* | 6.25 |

The A-32887 compounds are also antiviral agents. For example, A-32887 is active against type B influenza virus (Maryland, dog kidney), Transmissible Gastroenteritis virus and Infectious Canine Hepatitis virus, as demonstrated by in vitro plaque suppression tests, similar to that described by Siminoff, *Applied Microbiology* 9 [1], 66–72 (1961).

The acute toxicity of A-32887 (Na-K salt), when administered intraperitoneally to mice and expressed as $LD_{50}$, is 37.5 mg/kg × 1.

A most important property of the A-32887 compounds is their anticoccidial activity. For example, feeding experiments show that A-32887 (Na-K salt), when present in the feed of young chickens at levels as low as 40 ppm, decreases mortality and the number of lesions in chicks which have been challenged with coccidia. Tables XI through XIII summarize the results of tests with A-32887 (Na-K salt) in chicks challenged with various *Eimeria* species.

TABLE XI

| | | | | | Average Lesion Score | |
|---|---|---|---|---|---|---|
| Treatment [2,3] | PPM | Mortality[4] | Average Weight Gain (g)[5] | Feed/Gain[6] | Total Intestinal | Cecal |
| Normal Controls | 0 | 0 | 195 | 1.65 | 0 | 0 |
| Infected Controls | 0 | 40 | 66 | — | 10.8 | 3.7 |
| A-32887 (Na-K salt) | 100 | 0 | 159 | 1.87 | 1.6 | 0 |
| A-32887 (Na-K salt) | 80 | 0 | 182 | 1.83 | 3.0 | 0.3 |
| A-32887 (Na-K salt) | 60 | 0 | 155 | 1.83 | 5.9 | 0.6 |
| A-32887 (Na-K salt) | 40 | 0 | 176 | 1.89 | 4.9 | 1.6 |

ACTIVITY OF A-32887 AGAINST *E. tenella* AND *E. maxima*[1]

[1] 70,000 oocysts/bird of each of *E. tenella* and *E. maxima*
[2] Infected 48 hours postmedication; terminated seven days postinoculation
[3] Four replicates; five birds/replicate
[4] Due to coccidiosis
[5] Per survivor
[6] Pens without deaths only

TABLE XII

ACTIVITY OF A-32887 AGAINST *E. tenella* AND *E. acervulina*

| | | | | Average Lesion Score | | |
|---|---|---|---|---|---|---|
| Treatment | ppm | Percent Mortality[3] | Percent Weight Gain[4] | Intestinal | Cecal | Oocysts Per Bird ($1 \times 10^6$)[5] |
| Infected Controls | — | 12.5 | 63 | 1.2 | 3.6 | 29.37 |
| A-32887 (Na-K salt) | 121 | 0 | 73 | 0.3 | 0 | 0.4 |
| A-32887 (Na-K salt) | 100 | 0 | 85 | 0.6 | 0.1 | 1.28 |
| A-32887 (Na-K salt) | 77 | 0 | 90 | 0.7 | 0 | 5.48 |
| A-32887 (Na-K salt) | 62 | 0 | 97 | 0.9 | 0.1 | 16.40 |

[1] 6 replicates; 5 birds each
[2] Infection inoculum 48 hours post-medication onset
[3] Due to coccidiosis
[4] Normal controls = 100%
[5] Days 7–9

TABLE XIII

ACTIVITY OF A-32887 AGAINST *E. tenella*, *E. maxima* and *E. acervulina*

| Treatment[1,2] | ppm | Percent Mortality[3] | Percent Weight Gain[4] | Feed/Gain[5] | Average Lesion Score Intestinal | Cecal | Oocysts/Bird[6] $1 \times 10^6$ |
|---|---|---|---|---|---|---|---|
| Normal Controls | — | 0 | 100 | 1.46 | — | — | — |
| Infected Controls | — | 32.5 | 40 | — | 1.2 | 3.6 | 63.54 |
| A-32887 (Na-K salt) | 100 | 0 | 93 | 1.50 | 0 | 0.1 | 6.49 |
| A-32887 (Na-K salt) | 75 | 0 | 90 | 1.49 | 0.9 | 2.0 | 24.35 |
| A-32887 (Na-K salt) | 50 | 0 | 79 | 1.67 | 1.8 | 3.8 | 35.78 |
| A-32887 (Na-K salt) | 25 | 35 | 57 | — | 1.1 | 3.9 | 64.83 |

[1] 7 days post-inoculation; infection inoculum 24 hrs. post-medication onset
[2] Six replicates; 5 birds/each
[3] Due to coccidiosis
[4] Per survivor
[5] Pens without deaths, only
[6] Total days 5, 6 and 7 post-inoculation For the prevention or treatment of coccidiosis in poultry, a non-toxic anticoccidial amount of an A-32887 compound is administered to birds, preferably orally on a daily basis. The A-32887 compound can be supplied in many ways, but is is most conveniently supplied with a pharmaceutically-acceptable carrier, preferably the feed ingested by the birds. Although a variety of factors must be considered in determining an appropriate concentration of A-32887 compound, the rates of administration are generally in the range of about 30 to about 180 ppm in the feed and are preferably in the range of about 50 to about 120 ppm of feed ration.

This invention further relates to feed compositions adapted to protect poultry from coccidiosis and containing from about 45 to about 110 pounds of A-32887 compound per ton of poultry feed.

Another important property of the A-32887 compounds is their ability to improve feed-utilization efficiency in ruminants which have a developed rumen function. It is known that the efficiency of carbohydrate utilization in ruminants is increased by treatments which stimulate the animals' rumen flora to produce propionate compounds rather than acetate or butyrate compounds (for a more complete discussion see Church et al. in "Digestive Physiology and Nutrition of Ruminants", Vol. 2, 1971, pp 622 and 625).

The efficiency of feed use can be monitored by observing the production and concentration of propionate compounds in the rumen using the method described by Arthur P. Raun in U.S. Pat. No. 3,839,557 (see especially Example 6).

Table XIV shows the ratio of volatile-fatty-acid (VFA) concentrations in A-32887-treated flasks to concentrations in control flasks in this test.

TABLE XIV

| Compound | Dose(mcg/ml) | Ratio of Treated to Control | | | |
| --- | --- | --- | --- | --- | --- |
| | | Molar % Propionate | Molar % Acetate | Molar % Butyrate | Total VFA mM/l. |
| A-32887 (Na-K) | 1 | 1.4191* | 0.5744 | 1.1116 | 0.7498 |
| A-32887 (Na-K) | 10 | 1.2919* | 0.8857 | 0.7012 | 1.0086 |
| A-32887 Methyl Ether Derivative (Na-K) | 1 | 1.1219* | 0.9451 | 0.8166 | 1.1286 |
| A-32887 Methyl Ether Derivative (Na-K) | 5 | 1.2638* | 0.8997 | 0.7404 | 1.0693 |

*Statistically significant (P<0.01) by the two-tailed LSD test (R.G.D. Steel and J.H. Torrie, "Priciples and Procedures of Statistics", McGraw-Hill, New York, N.Y., 1960, p. 106)

Carbohydrate-utilization efficiency is further measured by in vivo tests performed in animals which have had a fistula installed in the rumen, making it possible to withdraw specimens of the rumen contents. The procedure used in testing cattle in this manner is also described in Raun's U.S. Pat. No. 3,839,557 (see Example 9). Table XV summarizes the results of such a test with A-32887 (Na-K salt) wherein five feed-lot cattle weighing approximately 425 kg. were in each group and the mean percent increases in ruminal propionate concentration were averaged over four analyses in a 24-day treatment period.

TABLE XV

| Treatment | Molar % Propionate | Molar % Acetate | Molar % Butyrate | Total VFA (mM/l.) |
| --- | --- | --- | --- | --- |
| Control | 17.4 | 74.5 | 8.1 | 79.9 |
| A-32887 (Na-K | 27.1* | 63.3* | 9.6 | 79.6 |

TABLE XV-continued

| Treatment | Molar % Propionate | Molar % Acetate | Molar % Butyrate | Total VFA (mM/l.) |
| --- | --- | --- | --- | --- |
| salt) 30 g/ton | | | | |

*Significantly different (P<0.01) from control by the two-tailed LSD test.

Table XVI summarizes the results of a similar test in sheep with A-32887 (Na-K salt) wherein four sheep were in each group and the mean percent increases in ruminal propionate concentration were averaged over four analyses in a 19-day treatment period.

TABLE XVI

| Treatment | Molar % Propionate |
| --- | --- |
| Control | 26.5 |
| A-32887 (Na-K salt) 15 g/ton | 29.5 |

The A-32887 compounds are typically effective in increasing propionates and, thereby, the efficiency of feed-utilization efficiency when administered to ruminants orally at rates of from about 0.07 mg/kg/day to about 4.0 mg/kg/day. Most beneficial results are achieved at rates of from about 0.2 mg/kg/day to about 2.0 mg/kg/day.

A preferred method of administration is to mix the A-32887 compound with the animals' feed; however, it can be administered in other ways, for example, tablets, drenches, sustained-release boluses, or capsules. Formulation of these various dosage forms can be accomplished by methods well known in the veterinary pharmaceutical art. Each individual dosage unit should contain a quantity of A-32887 compound directly related to the proper daily dose for the animal to be treated.

This invention further relates to feed compositions adapted to fatten cattle comprising cattle feed and from 1 to 25 grams per ton of an A-32887 compound.

In another aspect the A-32887 compounds are useful in the prevention and control of swine dysentery. A preferred method of administration to swine is by incorporation of an appropriate amount of an A-32887 compound into the feed ration. The results of tests with A-32887 (Na-K salt) when administered to pigs infected with acute swine dysentery are reported in Table XVII. In this test, groups of four pigs were challenged orally with 5.0 ml of a colon-content/tissue suspension prepared from pigs suffering from acute swine dysentery. Treated pigs were challenged 24 hours after initiating feed treatment. The test was carried out over a period of 26 days, observing pigs daily, and weighing them weekly and on day 26.

TABLE XVII

| Treatment | Final Average Wt. per Pig (lbs) | No. Died per No. in Group | Diarrhea Index* | No. with Colon Lesions/No. in Group |
|---|---|---|---|---|
| A-32887 (Na-K salt) 100 g/ton | 30.3 | 0/4 | 22 | 2/4 |
| Infected Non-medicated Controls | 14.3 | 3/4 | 53 | 4/4 |
| Infected Non-medicated Controls | 14.8 | 2/4 | 52 | 4/4 |

*Fecal material for each group was rated daily with 0= normal, 1= slight blood or mucus, 2= moderate blood or mucus, 3= marked blood or mucus. Index is the total score per treatment for 25 days.

The A-32887 compounds are also useful in the treatment of certain plant diseases. For example, A-32887 (Na-K salt), when applied at 400 ppm as a spray, inhibits powdery mildew disease in bean plants.

In another aspect, the A-32887 compounds are useful as insecticides. For example, A-32887 (Na-K salt) is active against insects such as Mexican bean beetle, Southern armyworm and housefly when applied at a rate of 1000 ppm.

Antibiotic A-32887 exhibits ion-binding and ion-transport properties and is, therefore, an ionophore (ion-bearer) (see B. C. Pressman, Alkali metal chelators — the ionophores, in "Inorganic Biochemistry," Volume 1, G. L. Eichhorn, Elsevier, 1973). A-32887 can be used when the selective removal of particular cations is desired. Examples of such uses include the removal and recovery of silver ions from solutions in photography, the removal of toxic cations from industrial waste streams before such streams are discharged to the environment, and desalinization of sea water. A-32887 can be used as one component of an ion-specific electrode (O. Kedem, et al., U.S. Pat. No. 3,753,887, Aug. 21, 1973, Alkali metal specific measuring electrode). A-32887 alters the cation permeability of both natural and artificial membranes. A-32887 can be used, therefore, as a component in a membrane used for the selective transport of cations against a concentration gradient. One potential application of this property is in recovery of heavy and precious metals on a commercial basis [see E. L. Cussler, D. F. Evans, and Sister M. A. Matesick, Science 172, 377 (1971)].

In yet another aspect, the A-32887 compounds are active as inhibitors of the enzyme ATPase. ATPase, an alkali-metal-sensitive enzyme found in cell membranes, is involved in the energy necessary for active transport. "Active transport" refers to the energy-requiring series of operations whereby intracellular and extracellular fluids maintain their compositions. Inhibitors of ATPase reduce the energy required for active transport. A-32887 (Na-K salt) has been shown to inhibit ATPase in in vitro tests using NaCl.

The A-32887 compounds are potential cardiotonic agents. In tests using guinea pig left atria, A-32887 (Na-K salt) increased cardiac contractility. Response to this test is expressed as a percentage of the maximal force that could be elicited by a challenge dose of norepinephrine. A-32887 (Na-K salt), at a $10^{-5}$ molar concentration, increased cardiac contractility by 28.0 ± 7.1 percent.

In order to illustrate more fully the operation of this invention, the following examples are provided:

EXAMPLE 1

A. Shake-flask Fermentation of A-32887

A lyophilized pellet of Streptomyces albus NRRL 11109 was dissolved in 1-2 ml of sterilized water. This solution was used to inoculate an agar slant having the following composition:

| Ingredient | Amount |
|---|---|
| Agar | 20 g |
| Dextrin | 10 g |
| Yeast extract | 1 g |
| Beef extract | 1 g |
| Enzymatic hydrolysate of casein* | 2 g |
| $CoCl_2 \cdot 6H_2O$ | 0.01 g |
| Deionized water | q.s. 1 liter |

NaOH was added to raise the pH of the medium from about 6.2 to about 7.0, before sterilizing; pH after sterilization about 6.9.
*NZ Amine A, Humko Sheffield Chemical, Lyndhurst, N.J.

The inoculated slant was incubated at 30° C. for about 7 days. The mature slant culture was scraped with a sterile pipette or loop to loosen the spores. About one-fourth of the loosened spores were used to inoculate 50 ml of a vegetative medium having the following composition:

| Ingredient | Amount |
|---|---|
| Glucose | 15 g |
| Soybean meal | 15 g |
| Corn steep liquor | 10 g |
| NaCl | 5 g |
| $CaCO_3$ | 2 g |
| Cold tap water | q.s. 1 liter |

The pH of this medium was adjusted from approximately 5.8 to about 6.5 by the addition of NaOH; post-sterilization pH about 6.5.

The inoculated vegetative medium was incubated in a 250-ml Erlenmeyer flask at 30° C. for about 48 hours on a shaker rotating through an arc two inches in diameter at 250 RPM.

This incubated vegetative medium (0.5–2.5 ml; 1–5%) was used to inoculate 50 ml of a production medium having the following composition:

| Ingredient | Amount (g/l.) |
|---|---|
| Glucose | 25.0 |
| Starch | 10.0 |
| Peptone* | 10.0 |
| Enzymatic-hydrolysate of casein** | 4.0 |
| Blackstrap molasses | 5.0 |
| $MgSO_4 \cdot 7H_2O$ | 0.5 |
| $CaCO_3$ | 2.0 |
| Czapek's mineral stock*** | |
| Deionized water | q.s. 1 liter |

*Wilson's Peptone 159, Wilsons' Protein Technology
**NZ Amine A, Humko Sheffield Chemical, Lyndhurst, N.J.
***Czapek's mineral stock has the following composition: 100 g KCl; 100 g $MgSO_4 \cdot 7H_2O$; 2 g $FeSO_4 \cdot 7H_2O$; q.s. to 1 liter with deionized water The inoculated production medium was incubated in a 250-ml Erlenmeyer flask at 30° C. for about 2 to 3 days on a shaker rotating through an arc two inches in diameter at 250 RPM.

B. Tank Fermentation of A-32887

In order to provide a larger volume of inoculum, 20 ml of incubated vegetative medium, prepared as described in Section A, was used to inoculate 400 ml of a second-stage vegetative-growth medium having the same composition as that of the vegetative medium. This second-stage vegetative medium was incubated in a 2-liter flask for about 24 hours at 30° C. on a shaker rotating through an arc two inches in diameter at 250 RPM.

Incubated second-stage medium (800 ml) thus prepared was used to inoculate 100 liters of sterile production medium, prepared as described in Section A. The inoculated production medium was allowed to ferment in a 165-liter fermentation tank for 3 to 4 days at a temperature of 30° C. The fermentation medium was aerated with sterile air at the rate of 0.25 V/V/M and was stirred with conventional agitators at 250 RPM.

EXAMPLE 2

Separation of A-32887

Whole fermentation broth (925 l.), obtained by the method described in Example 1, was adjusted to pH 8.5 by the addition of NaOH, stirred for 45 minutes, and filtered with a filter aid (Hyflo Super-cel, a diatomaceous earth, Johns-Manville Products Corp.). The filtered cake was washed with water, and the water wash was added to the filtered broth. The filtered-broth solution was then extracted twice with ethyl acetate (⅔ volumes). The ethyl acetate extracts were combined and concentrated under vacuum to give an oily residue. The residue was dissolved in benzene (4 l.); the benzene solution was filtered; and the filtrate was applied to a 9.5- × 162-cm silica-gel column (Grace, grade 62), prepared in benzene. After washing the column with benzene (24 l.), the eluting solvent was changed to benzene:ethyl acetate (3:2), collecting 37 liters consisting of fractions of 1 liter each. Elution was monitored by silica-gel thin-layer chromatography, using a benzene:ethyl acetate (1:1) solvent system and *Bacillus subtilis* bioautography for detection. The active fractions which contained A-32887 (11 l.) were combined and evaporated to dryness under vacuum. In order to remove color and other impurities, the residue thus obtained was dissolved in chloroform and chromatographed on a 2.2- × 40-cm column of carbon (Pittsburgh 12 × 40), prepared in chloroform. The column was washed with chloroform (3 l.); the chloroform eluate was concentrated to dryness under vacuum. The residue thus obtained was dissolved in diethyl ether (200 ml). The resulting solution was evaporated slowly under vacuum to give a thick syrup. The syrup was slowly warmed, and n-hexane (500 ml) was added with stirring. This solution was allowed to stand at room temperature until the A-32887 had crystallized. The crystalline A-32887 was separated by filtration and dried. The A-32887 was recrystallized by dissolving in acetone (500 ml), slowly adding water (200 ml), and allowing the resulting solution to stand at room temperature. The recrystallized A-32887 was separated by filtration, washed with water and dried to give 59 g of A-32887 Na-K salt. Further recrystallization gave additional A-32887 (Na-K salt) in the following amounts: 8.4 g in the second crop, and 5.2 g in the third crop (mp 158–160°).

EXAMPLE 3

Preparation of A-32887 Free Acid

A-32887 Na-K salt (1 g), obtained as described in Example 2, was dissolved in dioxane (200 ml). Water (25 ml) was added to this solution; the resulting solution was adjusted to pH 3 by the addition of dilute HCl. The acidified solution was stirred, and maintained at pH 3 with HCl, as water (100 ml) was slowly added. The resulting solution was evaporated under vacuum to remove the dioxane; the resulting aqueous suspension was extracted twice with ethyl acetate (equal volumes). The combined ethyl acetate extract was evaporated under vacuum to give an oily residue. This residue was dissolved in chloroform and re-evaporated under vacuum to give A-32887 free acid as a white amorphous powder (524 mg; mp about 90° C.)

EXAMPLE 4

Preparation of A-32887 Silver Salt

A-32887 Na-K salt (200 mg), obtained as described in Example 2, was dissolved in methanol (10 ml). An aqueous solution of silver nitrate (2 ml; 50 mg/ml) was added slowly. The resulting solution was placed in a beaker wrapped with aluminum foil to prevent degradation (reduction) of the silver. The solution was kept at 5° C. until crystallization was complete. The crystals were separated by filtration and were recrystallized from n-hexane to give A-32887 silver salt as very fine white needles (mp 166–168° C.).

EXAMPLE 5

Preparation of the Sodium Salt of A-32887

A-32887 free acid (500 mg), prepared as described in Example 3, was dissolved in acetone (150 ml); water (20 ml) was added. The resulting mixture was adjusted to pH 9 with NaOH. Water (200 ml) was then added, and the resulting solution was stirred for ½ hour. The solution was concentrated under vacuum to remove acetone. The resulting suspension was extracted with an equal volume of ethyl acetate. The ethyl acetate extract was concentrated under vacuum to dryness. The residue was dissolved in warm acetone (20 ml); water was added until the solution was turbid; and the solution was then allowed to crystallize. The crystals were removed by filtration, washed with water, and dried to give 306 mg of A-32887 sodium salt (mp 130°–133° C.).

EXAMPLE 6

Preparation of the Methyl Ether Derivative of A-32887

A-32887 free acid (3 g), prepared as described in Example 3, was dissolved in methanol (300 ml) and allowed to stand at room temperature for 12 hours. The conversion was monitored by silica-gel TLC, using a benzene:ethyl acetate (1:1) solvent system and $H_2SO_4$ spray for detection. The solution was evaporated to dryness under vacuum. The residue obtained was dissolved in benzene (40 ml). This solution was applied to a 3.2- × 95-cm column of silica gel (Grace, grade 62) packed in benzene. The column was eluted with benzene:ethyl acetate (3:2), collecting 25-ml fractions, and monitoring elution by TLC. Fractions 90–220, which contained most of the desired product, were combined and evaporated under vacuum to dryness. The residue, dissolved in benzene (15 ml) was rechromatographed on a 1.8- × 112-cm column of silica gel (Grace, grade 62), prepared in benzene. The column was eluted with benzene:ethyl acetate (9:1), collecting 25-ml fractions and monitoring elution by TLC. At fraction 383, the eluting solvent was changed to benzene:ethyl acetate (4:1); and at fraction 780 the solvent was changed to benzene:ethyl acetate (7:3). Fractions 450-700 contained A-32887; fractions 702-760 contained a mixture of A-32887 and A-32887 methyl ether derivative; and fractions 761-1130 contained A-32887 methyl ether derivative. Fractions 761-1130 were combined and evaporated to dryness under vacuum. The residue was dissolved in ethyl acetate (20 ml); n-hexane (80 ml) was added; and the solution was allowed to crystallize. The crystals were removed by filtration and dried to give 242 mg of A-32887 methyl ether derivative as the sodium salt (mp 214°-216° C.).

EXAMPLE 7

Preparation of the Acetyl Ester Derivative of A-32887

A-32887 Na-K salt (200 mg), prepared as described in Example 2, was dissolved in pyridine (8 ml); acetic anhydride (3.2 ml) was added. The mixture was allowed to stand overnight and then was evaporated under vacuum to dryness. The residue was dissolved in t-butanol and lyophilized to give 231 mg of the acetyl ester derivative of A-32887 (Na-K salt) as a white amorphous powder, mp 127°-129° C.

EXAMPLE 8

Preparation of the n-Butyryl Ester Derivative of A-32887

A-32887 (Na-K salt; 200 mg) was dissolved in pyridine (14 ml), and n-butyric anhydride (14 ml) was added. The mixture was allowed to stand for 17 hours at room temperature; water (14 ml) was added; and the solution was then concentrated to an oil in vacuo. The oily residue was lyophilized from dioxane-water several times to give 240 mg of the n-butyryl ester derivative of A-32887 (Na-K salt) as a white amorphous powder, mp 59°-62° C.

EXAMPLE 9

A-32887-Modified Chick Ration for Coccidiosis Control

A balanced, high-energy ration adapted to feed chicks for rapid weight gain is prepared by the following recipe:

| Ingredient | % | lbs |
|---|---|---|
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K, and $B_{12}$, choline, niacin, pantothenic acid, riboflavin, biotin, with glucose bulking agent) | 0.5 | 10 |
| Trace mineral premix (representing $MnSO_4$, ZnO, KI, $FeSO_4$, $CaCO_3$) | 0.2 | 4 |
| 2-Amino-4-hydroxybutyric acid (hydroxy analog of methionine) | 0.1 | 2 |
| A-32887 (Na-K Salt) | 0.01 | 0.2 |

These substances are mixed in accordance with standard feed-mixing techniques. Chicks fed such a ration, with water ad libitum, are protected against exposure to coccidiosis; weight gains are comparable to those of coccidiosis-free chicks fed a similar, unmedicated diet.

EXAMPLE 10

A-32887-Improved Beef-Cattle Ration

A balanced high-grain beef-cattle ration is prepared as follows:

| Ingredient | % | lbs |
|---|---|---|
| Finely ground corn | 67.8 | 1356 |
| Ground corn cob | 10 | 200 |
| Dehydrated alfalfa meal, 17 percent protein | 5 | 100 |
| Dehulled soybean meal, solvent extracted, 50 percent protein | 9.9956 | 199.912 |
| Cane molasses | 5 | 100.0 |
| Urea | 0.6 | 12.0 |
| A-32887 (Na-K salt) | 0.0044 | 0.088 |
| Dicalcium phosphate, feed grade | 0.5 | 10.0 |
| Calcium carbonate | 0.5 | 10.0 |
| Sodium chloride | 0.3 | 6.0 |
| Trace mineral premix | 0.03 | 0.6 |
| Vitamin A and $D_2$ premix* | 0.07 | 1.4 |
| Vitamin E premix** | 0.05 | 1.0 |
| Calcium propionate | 0.15 | 3.0 |

*Containing per pound: 2,000,000 I.U. of vitamin A; 227,200 I.U. of vitamin $D_2$ and 385.7 g. of soybean feed with 1% oil added
**Corn distillers dried grains with solubles containing 20,000 I.U. of d-alpha-tocopheryl acetate per pound The mixed feed is compressed into pellets. At an average daily ingestion rate of 15 pounds of feed per animal, this feed supplies approximately 300 mg. of A-32887 (Na-K salt) per animal per day.

EXAMPLE 11

A-32887-Improved Swine Ration

A balanced swine ration is prepared as follows:

| Ingredient | % | lbs./ton |
|---|---|---|
| Corn, Yellow, Ground | 73.15 | 1463 |
| Soybean Oil Meal, Solvent Extracted, Dehulled, 50% | 12.30 | 246 |
| Alfalfa Meal, Dehydrated, 17% | 2.50 | 50 |
| Meat Scraps, 55% | 2.50 | 50 |
| Fish Meal | 2.50 | 50 |
| Distiller Dried Solubles (Corn) | 2.50 | 50 |
| Animal Fat | 2.00 | 40 |
| Calcium Carbonate | 0.70 | 14 |
| Dicalcium Phosphate, Feed Grade | 0.50 | 10 |
| NaCl | 0.50 | 10 |
| Swine Vitamin Premix[1] | 0.50 | 10 |
| Methionine Hydroxy Analog, 93% | 0.20 | 4 |
| Trace Mineral Premix[2] | 0.10 | 2 |
| Selenium Premix[3] | 0.05 | 1 |
| Total | 100.00 | 2000 |

[1]Each kg of premix contains the following: 77,161 IU Vitamin $D_2$; 2,205 IU Vitamin E; 411 mg riboflavin; 1,620 mg pantothenic acid; 2,205 mg niacin; 4.4 mg Vitamin $B_{12}$; 441 mg Vitamin K; 19,180 mg choline; 110 mg folic acid; 165 mg pyridoxine; 110 mg thiamine; 22 mg biotin.
[2]Each kg of premix contains the following: 50 g manganese as manganese sulfate; 100 g zinc as zinc carbonate; 50 g iron as ferrous sulfate; 5 g copper as copper oxide; 1.5 g iodine as potassium iodide and 150 g maximum and 130 g minimum calcium as calcium carbonate.
[3]Each kg of premix contains 200 mg of selenium as sodium selenite.

A-32887 (Na-K salt; 100 g) is mixed with from about 5 to about 10 lbs. of soybean mill run to give a feed premix. From 5-10 lbs of this A-32887 premix is thoroughly mixed with a sufficient amount of the above-described swine ratio to give a concentration of 100 g of A-32887 per ton of ration. Swine fed such a ration, with water ad libitum, are protected against the lethal effects of swine dysentery.

We claim:

1. A method of increasing feed-utilization efficiency in ruminant animals which comprises orally administering to an animal in need thereof an effective propionate-increasing amount of a compound selected from the group consisting of (1) antibiotic A-32887, which in its free acid form is a white amorphous powder melting at about 90° C. and having the following characteristics:

(a) a molecular weight of about 946, as determined by mass spectrometry;
   (b) an approximate empirical formula of $C_{48-49}H_{80-86}O_{17-18}$ and a preferred empirical formula of $C_{48}H_{82}O_{18}$;
   (c) an approximate percentage elemental composition of 61.61% carbon, 8.56% hydrogen, and 28.63% oxygen;
   (d) an infrared absorption spectrum in chloroform with significant absorption maxima at the following frequencies ($cm^{-1}$): 3540 (shoulder), 3420 (medium), 2945 (shoulder), 2905 (strong), 2860 (shoulder), 2805 (shoulder), 1710 (weak), 1450 (medium), 1370 (medium), 1350 (shoulder), 1300 (shoulder), 1275 (weak), 1170 (shoulder), 1155 (medium), 1100 (shoulder), 1085 (strong), 1060 (strong), 1010 (weak), 990 (weak), 980 (shoulder), 948 (medium), 890 (weak), and 850 (weak);
   (e) no significant absorption in the ultraviolet spectrum;
   (f) a proton-magnetic-resonance spectrum which indicates the presence of five methoxyl groups;
   (g) a specific rotation as follows: $[\alpha]_D^{25} + 15.9°$ (c 1, $CHCl_3$);
   (h) an acid function capable of forming salts and ester derivatives;
   (i) at least one hydroxyl group capable of esterification;

and which in its mixed sodium-potassium salt form is a white crystalline compound, when crystallized from acetone-water, having the following characteristics:

(a') a melting point of about 187°-190° C.;
   (b') an approximate percentage elemental composition of 60.14% carbon, 8.11% hydrogen, 29.64% oxygen, 2.31% sodium, and 0.46% potassium;
   (c') an infrared absorption spectrum in chloroform with significant absorption maxima at the following frequencies ($cm^{-1}$): 3400 (shoulder), 3210 (medium), 2970 (strong), 2925 (strong), 2870 (weak), 2820 (weak), 1605 (medium), 1455 (medium), 1375 (shoulder), 1358 (medium), 1310 (weak), 1285 (weak), 1183 (medium), 1160 (medium), 1110 (shoulder), 1090 (strong), 1060 (strong), 1012 (weak), 980 (medium), 942 (medium), 910 (weak), 875 (shoulder), and 858 (weak);
   (d') an X-ray powder diffraction pattern (CuNi, 1.5405 λ, d=interplanar spacing in angstroms) as follows:

| d | Relative Intensity |
|---|---|
| 12.53 | 50 |
| 10.10 | 100 |
| 9.75 | 40 |
| 9.05 | 40 |
| 8.07 | 70 |
| 7.16 | 100 |
| 6.77 | 100 |
| 6.48 | 70 |
| 6.16 | 60 |
| 5.58 | 50 |
| 5.35 | 50 |
| 5.10 | 30 |
| 4.86 | 60 |
| 4.70 | 50 |
| 4.44 | 50 |
| 4.25 | 50 |
| 4.06 | 40 |
| 3.80 | 30 |
| 3.68 | 40 |
| 3.58 | 30 |
| 3.42 | 60 |
| 3.22 | 10 |
| 3.06 | 10 |
| 2.97 | 10 |
| 2.85 | 10 |
| 2.76 | 02 |
| 2.61 | 15 |
| 2.49 | 05 |
| 2.47 | 05 |
| 2.44 | 15 |
| 2.36 | 10 |
| 2.29 | 10 |
| 2.20 | 02 |
| 2.12 | 02 |
| 2.03 | 05 |
| 1.96 | 05 |
| 1.90 | 02 |
| 1.81 | 02 |

(e') a specific rotation as follows: $[\alpha]_D^{25} + 9.6°$ (c 1, $CHCl_3$);
   (f') a titratable group in 80% aqueous dimethylformamide with a pKa value of 4.60;
   (g') solubility in methanol, ethanol, dimethylformamide, dimethyl sulfoxide, ethyl acetate, chloroform, acetone, and benzene; slight solubility in hexane; and insolubility in water;
   (h') stability in aqueous solutions having a pH of from about 3 to about 11, instability in solutions having a pH lower than about 3;
   (i') approximate $R_f$ values in the following paper-chromatographic systems using Bacillus subtilis ATCC 6633 bioautography for detection:

| Solvent System | $R_f$ Value |
|---|---|
| Water saturated with methyl isobutyl ketone (MIBK) | 0.58 |
| Water:methanol:acetone (12:3:1). This solution is adjusted to pH 10.5 with $NH_4OH$ and then lowered to pH 7.5 with $H_3PO_4$ | 0.32 |
| Propanol:water (1:9) | 0.85 |
| Methanol:propanol:water (6:2:1). Paper buffered with 0.75 M $KH_2PO_4$, pH 4.0. | 0.79 |
| Methanol:0.05 M sodium citrate at pH5.7 (7:3). Paper buffered with 0.05 M sodium citrate at pH 5.7. | 0.85 |
| Propanol:water (7:3) | 0.91 |

(j') approximate $R_f$ values in the following thin-layer chromatographic systems, using either vanillin spray reagent or Bacillus subtilis bioautography for detection:

| Solvent System | $R_f$ Value |
| --- | --- |
| Methanol | 0.80 |
| Ethyl acetate:ethanol (1:4) | 0.65 |
| Ethyl acetate:chloroform (1:1) | 0.36 |
| Ethyl acetate:chloroform (6:1) | 0.67 |
| Benzene:ethyl acetate:methanol (6:4:0.2) | 0.58 | and which in its sodium salt form has a molecular weight of about 968 and in its potassium salt form has a molecular weight of about 984, both as determined by FD mass spectrometry; and which in its silver salt form is a crystalline compound (from n-hexane) with a melting point of 166°–168° C.; (2) the acetyl ester derivative of antibiotic A-32887, having an approximate empirical formula of $C_{50-51}H_{82-88}O_{18-19}$, and which in its Na-K salt form has a molecular weight of about 988, a melting point of about 127°–129° C., and an approximate $R_f$ value of 0.40 on silica-gel TLC in benzene:ethyl acetate (1:1), and an infrared absorption spectrum as shown in FIG. 4 of the drawings; (3) the n-butyryl ester derivative of antibiotic A-32887, having an approximate empirical formula of $C_{52-53}H_{86-92}O_{18-19}$, and which in its Na-K salt form has a molecular weight of about 1016, a melting point of about 59°–62° C., an approximate $R_f$ value of 0.64 on silica-gel TLC in benzene:ethyl acetate (1:1), and an infrared absorption spectrum as shown in FIG. 5 of the drawings; and (4) the pharmaceutically-acceptable salts thereof.

2. The method of claim 1 wherein the compound is antibiotic A-32887 or a pharmaceutically-acceptable salt thereof.

3. The method of claim 2 wherein the compound is antibiotic A-32887 Na-K salt.

4. A method of increasing feed-utilization efficiency in ruminant animals which comprises orally administering to an animal in need thereof an effective propionate-increasing amount of a compound selected from the group consisting of (1) the methyl ether derivative of A-32887, having a molecular weight of about 960 and an approximate empirical formula of $C_{49-50}H_{82-88}O_{17-18}$, and which in its sodium salt form is a white crystalline compound, when crystallized from n-hexane: ethyl acetate, having a melting point of about 214°–216° C. and having the following characteristics:

(a) a molecular weight of about 982, as determined by FD mass spectrometry;

(b) an infrared absorption spectrum in chloroform with significant absorption maxima at the following frequencies (cm$^{-1}$): 3400 (broad), 2990, 2960, 2930, 2870, 2820, 1725, 1610, 1455, 1407, 1370, 1309, 1282, 1240, 1180, 1158, 1110, 1093, 1082, 1057, 1010, 980, 945, 900, 868, 858, 827, 802, 700, and 653;

(c) a proton-magnetic-resonance spectrum which indicates the presence of six methoxyl groups;

(d) a specific rotation as follows: $[\alpha]_D^{25} - 5.1°$ (c 1, CHCl$_3$);

(e) an X-ray powder diffraction pattern (CuNi, 1.5405 λ, d = interplanar spacing in angstroms) as follows:

| d | Relative Intensity |
| --- | --- |
| 13.18 | 50 |
| 12.01 | 50 |
| 9.02 | 100 |
| 8.26 | 100 |
| 7.19 | 80 |
| 6.46 | 50 |
| 5.78 | 20 |
| 5.46 | 20 |
| 5.00 | 30 |
| 4.24 | 20 |
| 3.72 | 20 |
| 3.36 | 05 |

(f) a titratable group in 80% aqueous dimethylformamide with a p$K_a$ value of about 5.4;

(g) solubility in methanol, ethanol, dimethylformamide, dimethyl sulfoxide, ethyl acetate, chloroform, acetone, and benzene; slight solubility in hexane and heptane; and insolubility in water;

(h) an acid function capable of forming salts and ester derivatives; and (2) the pharmaceutically-acceptable salts of the A-32887 methyl ether derivative.

5. The method of claim 4 wherein the compound is A-32887 methyl ether derivative sodium salt.

* * * * *